US005607672A

United States Patent [19]
Hillman

[11] Patent Number: 5,607,672
[45] Date of Patent: Mar. 4, 1997

[54] REPLACEMENT THERAPY FOR DENTAL CARIES

[75] Inventor: Jeffrey D. Hillman, Gainesville, Fla.

[73] Assignee: University of Florida Research Foundation, Inc., Gainesville, Fla.

[21] Appl. No.: 486,037

[22] Filed: Jun. 7, 1995

[51] Int. Cl.$^6$ ............................ C12N 1/21; C12N 15/53; A01N 63/00; A61K 7/16
[52] U.S. Cl. .................................. 435/172.3; 435/252.3; 424/93.44; 424/50
[58] Field of Search ............................ 435/252.3, 172.3; 424/93.44, 50

[56] References Cited

U.S. PATENT DOCUMENTS

| | | |
|---|---|---|
| 4,133,875 | 1/1979 Hillman | 424/93 |
| 4,324,860 | 4/1982 Hillman | 435/172 |

OTHER PUBLICATIONS

Jordan, "Bacteriological Aspects of Experimental Dental Caries," *Ann. N.Y. Acad. Sci.*, 131:905–912, (1965).
Gibbons et al., "Dextran–induced Agglutination of *Streptococcus mutans*, and its Potential Role in the Formation of Microbial Dental Plaques," *J. Bacteriol.*, 98:341–346, (1969).
Carlsson et al., "Chemically Defined Medium for Growth of *Streptococcus sanguis*," *Caries Res.*, 4:297–304, (1970).
Makinen et al., "The Role of Sucrose and Other Sugars in the Development of Dental Caries; A Review," *Int. Dent. J.*, 22:364–386, (1972).
Yamada et al., "Regulation of Lactate Dehydrogenase and Change of Fermentation Products in Streptococci," *J. Bacteriol.*, 124(1):55–61, (1975).
Hillman, "Lactate Dehydrogenase Mutants of *Streptococcus mutans*: Isolation and Preliminary Characterization," *Infect. Immun.*, 21(1):206–212, (1978).
Hamilton et al., "Lactose Metabolism by *Streptococcus mutans*: Evidence for Induction of the Tagatose 6–Phosphate Pathway," *J. Bacteriol.*, 140(8): 1102–1104, (1979).
Perry et al., "Genetic Transformation of *Streptococcus mutans*," *Infect. Immun.*, 32(3):1295–1297, (1981).
Wasserman et al., "Catabolic Alanine Racemase from *Salmonella typhimurium*: DNA Sequence, Enzyme Purification and Characterization," *Biochem.*, 23:5182–7, (1984).
Tobian et al., "Characterization and Expression of a Cloned Tetracycline Resistance Determinant from the Chromosome of *Streptococcus mutans*," *J. Bacteriol.*, 160(2):556–563, (1984).
Hillman et al., "Isolation of a *Streptococcus mutans* Strain Producing a Novel Bacteriocin," *Infect. Immun.*, 44(1): 141–144, (1984).
Abhyankar et al., "Serotype c *Streptococcus mutans* Mutatable to Lactate Dehydrogenase Deficiency," *J. Dent. Res.*, 64:1267–1271, (1985).
Ferrari et al., "Isolation of an Alanine Racemase Gene From *Bacillus Subtilis* and its Use for Plasmid Maintenance in *B. Subtilis*," *Biotechnol. (NY)*, 3:1003–7, (1985).

Neale et al., "The Two Alcohol Dehydrogenases of *Zymomonas mobilis*," *Eur. J. Biochem.*, 154:119–124, (1986).
Galakatos et al., "Biosynthetic *alr* Alanine Racemase from *Salmonella typhimurium*: DNA and Protein Sequence Determination," *Biochem.*, 25:3255–60, (1986).
Youngman, "Plasmid vectors for recovering and exploiting Tn917 transpositions in Bacillus and other Gram–positive bacteria," *Plasmids: A Practical Approach*, Hardy, ed., IRL Press, Oxford, pp. 79–103, (1987).
Conway et al., "Cloning and Sequencing of the Alcohol Dehydrogenase II Gene from *Zymomonas mobilis*," *J. Bacteriol.*, 169(6):2591–2597, (1987).
Conway et al., "Promoter and Nucleotide Sequences of the *Zymomonas mobilis* Pyruvate Decarboxylase," *J. Bacteriol.*, 169(3):949–954, (1987).
Hillman et al., "Colonization of the Human Oral Cavity by a *Streptococcus mutans* Mutant Producing Increased Bacteriocin," *J. Dent. Res.*, 66:1092–1094, (1987).
Hillman et al., "Acetoin Production by Wild–Type Strains and a Lactate Dehydrogenase–Deficient Mutant of *Streptococcus mutans*," *Infect. Immun.*, 55(6):1399–1402, (1987).
Lee et al., "Molecular Cloning and Expression of a *Streptococcus mutans* Major Surface Protein Antigen, P1 (I/II), in *Escherichia coli*," *Infect. Immun.*, 56:2114–2119, (1988).
Tanizawa et al., "Thermostable Alanine Racemase from *Bacillus stearothermophilus*: DNA and Protein Sequence Determination and Secondary Structure Prediction," *Biochem.*, 27:1311–16, (1988).
Lee et al., "Construction and Characterization of Isogenic Mutants of *Streptococcus mutans* Deficient in Major Surface Protein Antigen P1 (I/II)," *Infect. Immun.*, 57(11):3306–3313, (1989).
Hillman et al., "The Theory and Application of Bacterial Interference to Oral Diseases," *New Biotechnologies in Oral Research*, H.M. Myers, ed., S. Karger, Basel, Switzerland, pp. 1–17, (1989).
Hillman et al., "Cloning and Expression of the Gene Encoding the Fructose–1,6–Diphosphate–Dependent L–(+)–Lactate Dehydrogenase of *Streptococcus mutans*," *Infect. Immun.*, 58(5):1290–1295, (1990).
Camilli et al., "Insertional Mutagenesis of *Listeria monocytogenes* with a Novel Tn917 Derivative That Allows Direct Cloning of DNA Flanking Transposon Insertions," *J. Bacteriol.*, 172:3738–3744, (1990).
Duncan et al., "DNA Sequence and In Vitro Mutagenesis of the Gene Encoding the Fructose–1,6–Diphosphate–Dependent L–(+)–Lactate Dehydrogenase of *Streptococcus mutans*," *Infect. Immun.*, 59(11):3930–3934, (1991).
Leenhouts et al., "Nucleotide Sequence and Characterization of the Broad–Host–Range Lactococcal Plasmid pWV01," *Plasmid*, 26:55–66, (1991).

(List continued on next page.)

Primary Examiner—Charles L. Patterson, Jr.
Attorney, Agent, or Firm—Fish and Richardson P.C.

[57] ABSTRACT

Recombinant *Streptococcus mutans* strains characterized by a deficiency in lactic acid production and production of a recombinant alcohol dehydrogenase (ADH) are described, These recombinant *S. mutans* strains are suitable for use in a method for preventing treating dental caries.

36 Claims, 4 Drawing Sheets

OTHER PUBLICATIONS

Lobocka, "Organization and Expression of the *Eschericha coli* K–12 *dad* Operon Encoding the Smaller Subunit of D–Amino Acid Dehydrogenase and the Catabolic Alanine Racemase," *J. Bacteriol.*, 176:1500–10, (1994).

Chen et al., "L–(+)–Lactate Dehydrogenase Deficiency is Lethal in *Streptococcus mutans*," *J. Bacteriol.*, 176(5):1542–1545, (1994).

Hillman et al., "Evidence that L–(+)–Lactate Dehydrogenase Deficiency is Lethal in *Streptococcus mutans*," *Infect. Immun.*, 62(1):60–64, (1994).

Crowley et al., "Analysis of Genetic Regulation of a Major Cell Surface Adhesin Gene (*spaP*) from *Streptococcus mutans*," *J. Dent. Res.*, 74, Abstract No. 1511, (1995).

MASSTFYIPFVNEMGEGSLEKAIKDLNGSGFKNALIVSDAFMNK

SGVVKQVADLLKAQGINSAVYDGVMPNPTVTAVLEGLKILKDNNSDFVISLGGGSPHD

CAKAIALVATNGGEVKDYEGIDKSKKPALPLMSINTTAGTASEMTRFCIITDEVRHVK

MAIVDRHVTPMVSVNDPLLMVGMPKGLTAATGMDALTHAFEAYSSTAATPITDACALK

AASMIAKNLKTACDNGKDMPAREAMAYAQFLAGMAFNNASLGYVHAMAHQLGGYYNLP

HGVCNAVLLPHVLAYNASVVAGRLKDVGVAMGLDIANLGDKEGAEATIQAVRDLAASI

GIPANLTELGAKKEDVPLLADHALKDACALTNPRQGDQKEVEELFLSAF (SEQ ID NO:1)

FIG. 1a

```
   1  aaaggcaaaa  tcggtaacca  catctcaatt  attaaacaat  acttcataat  aaaagacaa
  61  cttttcata   atttgcataa  gtcttgatgt  aaaaaataca  tatttagaaa  gaacaagcag
 121  ccttgctcat  caccgctgtc  gcgagtagaa  aaatctcggc  tttcagaaaa  agaggccgct
 181  tcgttaaaca  gactataaat  gtgctggaat  aaagcgaacc  ccttgatctg  ataaaactga
 241  tagacatatt  gcttttgcgc  tgcccgattg  ctgaaaatgc  gtaaaaggtg  attttactcg
 301  ttttcaggaa  aaactttgag  aaaacgtctc  gaaaacggga  ttaaaacgca  aaaacaatag
 361  aaagcgattt  cgcgaaaatg  gttgttttcg  ggttgttgct  ttaaactagt  atgtagggtg
 421  aggttatagc  tatggcttct  tcaacttttt  atattccttt  cgtcaacgaa  atgggcgaag
 481  gttcgcttga  aaaagcaatc  aaggatctta  acggcagcgg  ctttaaaaat  gcgctgatcg
 541  tttctgatgc  tttcatgaac  aaatccggtg  ttgtgaagca  ggttgctgac  ctgttgaaag
 601  cacagggtat  taattctgct  gtttatgatg  gcgttatgcc  gaacccgact  gttaccgcag
 661  ttctggaagg  ccttaagatc  ctgaaggata  acaattcaga  cttcgtcatc  tccctcggtg
 721  gtggttctcc  ccatgactgc  gccaaagcca  tcgctctggt  cgcaaccaat  ggtggtgaag
 781  tcaaagacta  cgaaggtatc  gacaaatcta  agaaacctgc  cctgcctttg  atgtcaatca
 841  acacgacggc  tggtacggct  tctgaaatga  cgcgtttctg  catcatcact  gatgaagtcc
 901  gtcacgttaa  gatggccatt  gttgaccgtc  acgttacccc  gatggtttcc  gtcaacgatc
 961  ctctgttgat  ggttggtatg  ccaaaaggcc  tgaccgccgc  caccggtatg  gatgctctga
1021  cccacgcatt  tgaagcttat  tcttcaacgg  cagctactcc  gatcaccgat  gcttgcgcct
1081  tgaaggctgc  gtccatgatc  gctaagaatc  tgaagaccgc  ttgcgacaac  ggtaaggata
1141  tgccagctcg  tgaagctatg  gcttatgccc  aattcctcgc  tggtatggcc  ttcaacaacg
1201  cttcgcttgg  ttatgtccat  gctatggctc  accagttggg  cggctactac  aacctgccgc
1261  atggtgtctg  caacgctgtt  ctgcttccgc  atgttctggc  ttataacgcc  tctgtcgttg
1321  ctggtcgtct  gaaagacgtt  ggtgttgcta  tgggtctcga  tatcgccaat  ctcggtgata
1381  aagaaggcgc  agaagccacc  attcaggctg  ttcgcgatct  ggctgcttcc  attggtattc
1441  cagcaaatct  gaccgagctg  ggtgctaaga  aagaagatgt  gccgcttctt  gctgaccacg
1501  ctctgaaaga  tgcttgtgct  ctgaccaacc  cgcgtcaggg  tgatcagaaa  gaagttgaag
1561  aactcttcct  gagcgctttc  taatttcaaa  acaggaaaac  ggttttccgt  cctgtcttga
1621  ttttcaagca  aacaatgcct  ccgatttcta  atcggaggca  tttgtttttg  ttattgcaa
1681  aaacaaaaa   tattgttaca  aattttaca   ggctattaag  cctaccgtca  taaataattt
1741  gccattt  (SEQ ID NO:2)
```

FIG. 1b

REPLACEMENT THERAPY FOR DENTAL CARIES

This invention was made at least in part with funds from the Federal government through a grant from the National Institute of Dental Research, Public Health Service grant no. DE04529. The government may have certain rights in this invention.

BACKGROUND OF THE INVENTION

1. Field of the Invention

This invention relates to methods and compositions for the prevention of dental caries.

2. Description of Related Art

The ability of a given bacterium to colonize a host is determined by a number of factors such as the bacterium's metabolic needs, and the interactions of the bacterium with the pre-existing bacterial flora. Bacterial interactions can be generally classified as either "positive" or "negative." In positive interactions, an "effector" bacterial strain alters the microenvironment to promote colonization of a second, "target" organism. In "negative" interactions, the effector strain alters the microenvironment in a manner that decreases or completely prevents target bacterium colonization. Negative interactions between competing bacteria during host colonization are commonly termed bacterial interference.

Therapeutic regimens which take advantage of bacterial interference to replace a pathogenic bacterial strain with a non-pathogenic, effector strain are termed replacement therapies. Successful replacement therapy requires an effector strain that: 1) is non-pathogenic, 2) alters the microenvironment so as to prevent colonization or outgrowth of pathogenic organisms, 3) persistently colonizes the host at risk to prevent reinfection by the target pathogenic organism, and aggressively displace the pathogenic organism from the tissues at risk where the pathogen is part of the host's indigenous flora.

It is well known that dental caries are caused by bacteria that colonize the oral cavity. The principle dental caries-causing bacterial pathogen in humans is the bacterium *Streptococcus mutans*. The characteristic features of *S. mutans* implicated in cariogenesis include its ability to produce lactic acid, as well as its ability to accumulate on tooth enamel (i.e., plaque formation) (Gibbons et al., 1969, *J. Bacteriol.*, 98.:341–346; Makinen et al., 1972, *Int. Dent. J.*, 22:362–386; and Jordan, 1965, *Ann. N.Y. Acad. Sci.*, 131:905–912). Application of the principles of replacement therapy would require the isolation of a non-cariogenic effector strain of *S. mutans*, e.g., a *S. mutans* strain deficient in lactic acid synthesis. The progress in the application of replacement therapy to dental caries has been recently reviewed (Hillman et al., 1989, In: *New Biotechnologies in Oral ReSearch*, H. M. Myers, ed., S. Karger, Basel, Switzerland, pgs. 1–17).

Generation of a lactic acid-deficient *S. mutans*, and thus a strain suitable for replacement therapy for dental caries, has met with considerable difficulty. Defects in lactic acid synthesis are lethal to *S. mutans*. Abhyanakar et al. (1985, *J. Dent. Res.*, 64:1267–1271) generated a lactate dehydrogenase(LDH)-deficient *S. mutans* mutant by chemical mutagenesis using an atypical *S. mutans* strain that contained a preexisting (spontaneous) mutation affecting pyruvate metabolism. However, the chemically-induced and the spontaneously-generated mutations in this strain remain uncharacterized. Moreover, chemically-induced, uncharacterized mutations can revert to wild-type, and thus the pathogenic, cariogenic phenotype. Subsequent attempts to produce LDH-deficiencies in other *S. mutans* strains have failed (Hillman et al., 1994, *Infect. Immun.*, 62:60–64; Chen et al., 1994, *J. Bacteriol.*, 176:1542–1545).

There is a clear need in the field for a stable, lactic acid-deficient, non-cariogenic strain of *S. mutans* that is suitable for use in a replacement therapy in the prevention and/or treatment of dental caries.

SUMMARY OF THE INVENTION

The invention is based on the discovery that lactic acid-deficient *Streptococcus mutans* strains can be generated by introducing a mutation in a gene involved in the lactic acid synthesis pathway, and preventing the lethality of this mutation by introducing a recombinant alcohol dehydrogenase (adh) gene into the lactic acid-deficient bacterium. The recombinant adh prevents accumulation of metabolites (e.g., pyruvate) in the bacterium, thus circumventing the lethality of the lactic acid deficiency. This strategy can be applied to production of a *S. mutans* strain suitable for use in a replacement therapy for dental caries.

In general, the invention features methods and compositions for the prevention and/or treatment of dental caries in a dental caries-susceptible host.

In one aspect, the invention features a recombinant *Streptococcus mutans* strain characterized by a deficiency in lactic acid production (e.g., due to elimination of lactate dehydrogenase activity) and, in its stead, production of a recombinant alcohol dehydrogenase (ADH). "Deficiency in lactic acid production" or "lactic acid deficient" means that the recombinant *S. mutans* strain produces substantially decreased amounts of lactic acid relative to wild-type *S. mutans*. Preferably, a "lactic acid deficient" recombinant *S. mutans* produces no detectable lactic acid. The invention also features methods for producing the recombinant strains of the invention.

A preferred recombinant *S. mutans* strain is characterized by: 1) a deficiency in lactic acid production; 2) production of a recombinant alcohol dehydrogenase; and 3) production of a bacteriocin having antibacterial activity against a bacteriocin-susceptible *Streptococcus mutans* strain, and 4) optionally can be auxotrophic (e.g., auxotrophic for D-alanine).

Additional preferred recombinant *S. mutans* strains are deficient in lactic acid production, produce a recombinant alcohol dehydrogenase, and are auxotrophic (e.g., auxotrophic for D-alanine).

The invention additionally features pharmaceutical compositions composed of a recombinant lactic acid-deficient, recombinant ADH-producing *S. mutans* strain and a pharmaceutically acceptable carrier.

The invention also features a method of reducing the incidence or severity of dental caries in a dental caries-susceptible host by orally administering to a dental caries-susceptible host a recombinant *Streptococcus mutans* strain having 1) a recombinant alcohol dehydrogenase gene and 2) a deficiency in lactic acid production, in an amount effective for replacement of dental caries-causing *Streptococcus mutans* host strains in the oral cavity of the host.

The invention additionally features a composition for maintenance of a D-alanine bacterial auxotroph (e.g., a *S. mutans* D-alanine auxotroph) in the oral cavity of a host comprising a D-alanine bacterial auxotroph-maintaining amount of D-alanine.

One advantage of the invention is that the recombinant *S. mutans* strains 1) are lactic acid deficient, and thus will not cause dental caries, and 2) will effectively replace dental caries-causing strains of *S. mutans* in the oral cavity of the host.

Another advantage is that, where the recombinant *S. mutans* is a D-alanine auxotroph, colonization of the strain can be controlled by administration of D-alanine.

Other features and advantages of the invention will be apparent from the following description of the preferred embodiments thereof, and from the claims.

BRIEF DESCRIPTION OF THE DRAWINGS

FIG. 1 shows the amino acid (SEQ ID NO:1) and DNA sequence (SEQ ID NO:2) of *Z. mobilis* alcohol dehydrogenase II.

DETAILED DESCRIPTION

Figure 2:
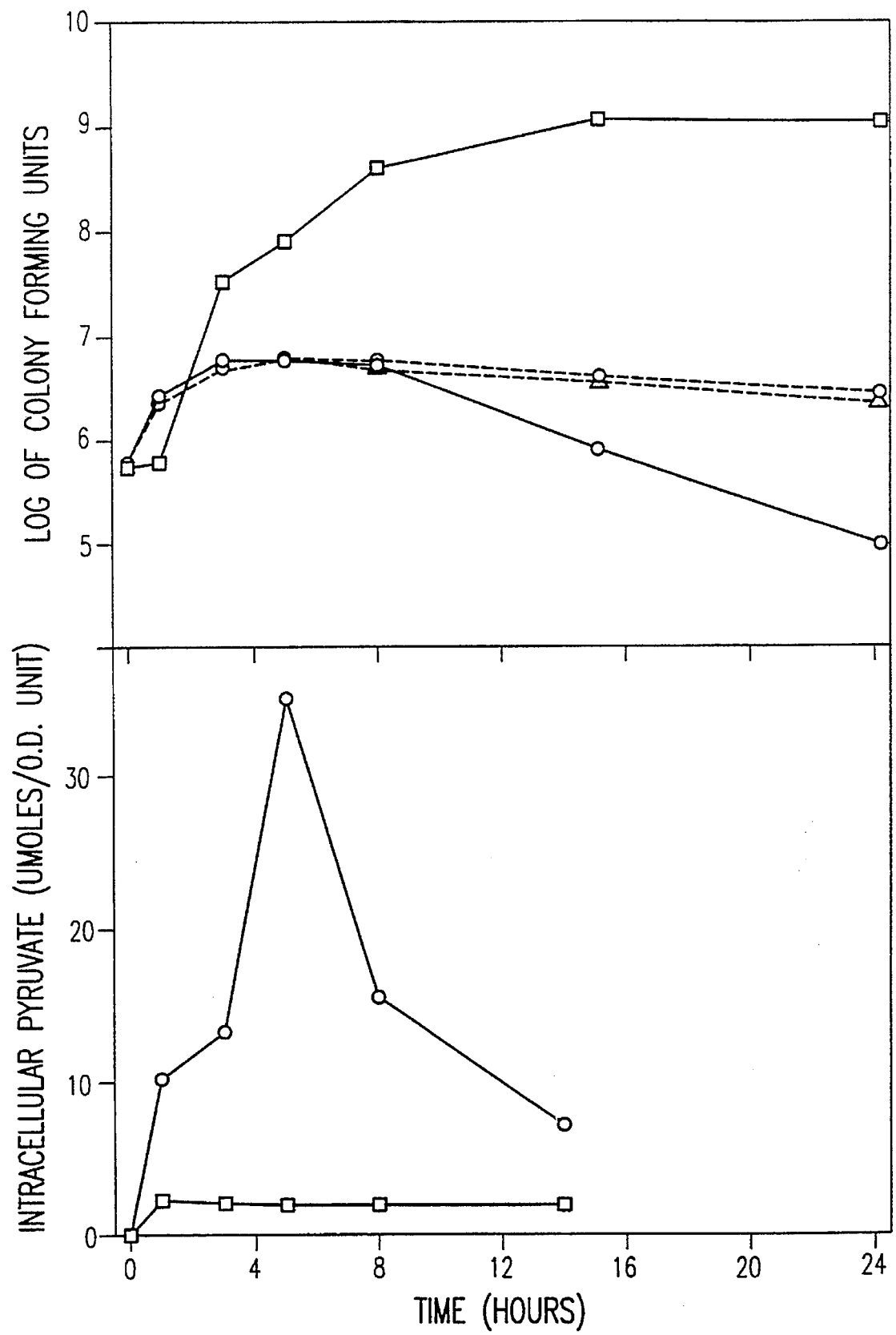
FIG. 2 shows the effect of glucose on the growth, survival, and intracellular pyruvate concentration of the *Streptococcus mutans* strains CH4ts and NG8 (control). Symbols: NG8 with glucose, —□—; NG8 without glucose, --o--; CH4ts with glucose, —o—; CH4ts without glucose, --Δ--.

Dental caries are caused by the production and accumulation of lactic acid by *Streptococcus mutans* that normally colonizes the oral cavity. However, since mutations in the lactic acid production pathway of *S. mutans* are lethal for the bacterium, introduction of lactic acid deficient *S. mutans* into the oral cavity to replace lactic acid-producing *S. mutans* strains has not been possible.

The invention is based on the discovery that viable, lactic acid-deficient *Streptococcus mutans* strains can be generated by transforming the strains with nucleic acid encoding a recombinant alcohol dehydrogenase (ADH), and introducing a mutation in the lactic acid synthesis pathway to render the recombinant ADH-producing strain lactic acid deficient. The recombinant ADH prevents accumulation of metabolites in the bacterium, thus circumventing the lethality of the lactic acid deficiency. This strategy can be applied to production of recombinant *S. mutans* strains suitable for use in a replacement therapy for dental caries.

Recombinant *Streptococcus mutans* strains of the invention

A "recombinant *Streptococcus mutans* strain" is a non-naturally occurring strain of *S. mutans* that has been generated using any of a variety of recombinant nucleic acid techniques (i.e., techniques involving the manipulation of DNA or RNA). In general, a recombinant *Streptococcus mutans* strain of the invention is minimally characterized by:

1) a deficiency in lactic acid production, and 2) production of a recombinant alcohol dehydrogenase (ADH).

Recombinant *S. mutans* strains are preferably further characterized by production of a bacteriocin having antibacterial activity against a bacteriocin-susceptible *S. mutans* strain. "Bacteriocin," as used herein, means the specific bacteriocin or bacteriocin-like toxin produced by *S. mutans* strain JH1000 (Hillman et al., 1984, *Infect. Immun.*, 44:141–144). The bacteriocin of *S. mutans* JH1000 has an apparent molecular weight of less than about 1,000 Da, and has antibacterial activity against bacteriocin-susceptible *S. mutans* strains. Production of the bacteriocin thus provides the *S. mutans* with a selective advantage over non-bacteriocin-producing *S. mutans* strains normally present in the oral cavity. The bacteriocin, when present in a recombinant *S. mutans* strain of the invention, eliminates the resident, bacteriocin-susceptible *S. mutans* strains, thus interfering with colonization of bacteriocin-susceptible strains and promoting recombinant *S. mutans* colonization of the oral cavity.

Because it may be desirable to control oral cavity colonization by the recombinant *S. mutans* strains of the invention, the recombinant *S. mutans* strain is preferably an auxotroph for an organic substance not normally present in the oral cavity of the mammalian host, more preferably an auxotroph for a D-amino acid, even more preferably a D-alanine auxotroph. Colonization of auxotrophic strains can be controlled by regulating the amount of the organic substance for which the strain has an auxotrophy. Thus, if the need arises to rid the host of recombinant *S. mutans*, colonization can be terminated by withholding administration of the specific organic substance for which the strain is auxotrophic.

Thus, recombinant *S. mutans* strains of the invention are characterized by: 1) a lactic acid deficiency, and 2) production of a recombinant ADH, and can be further characterized by 3) bacteriocin production, and/or 4) an auxotrophy for a specific organic substance, preferably a D-amino acid, more preferably D-alanine. Production of each of the recombinant *S. mutans* strains of the invention will now be described in detail.

Parent *Streptococcus mutans* strains for use in production of recombinant *S. mutans* strains of the invention The *Streptococcus mutans* strain for use in the production of recombinant *S. mutans* strains of the invention can be any *S. mutans* strain. Preferably, the *S. mutans* strain used to produce recombinant *S. mutans* strains of the invention have a selective advantage over wild-type *S. mutans* strains that normally colonize the oral cavity. The selective advantage can be conferred by any of a variety of characteristics (e.g., production of a antibacterial compound, relative metabolic needs, relative growth rate, production of scavengers for metabolites) that promote oral cavity colonization by the strain, and replacement of the resident strain colonizing the oral cavity. Preferably, colonization by the recombinant *S. mutans* strains of the invention will not substantially disrupt colonization by other, non-*S. mutans* strains (e.g., normal bacterial flora not associated with cariogenesis). For example, infection of human volunteers with a variant strain of *S. mutans* JH1000 that produced enhanced levels of bacteriocin resulted in replacement of the resident, cariogenic *S. mutans* strains (presumably in part due to bacteriocin production by the JH1000 strain) without effect upon other resident Gram positive species of the oral cavity (Hillman et al., 1987, *J. Dent. Res.*, 66:1092–1094).

Preferably, the *S. mutans* strain produces the bacteriocin of *S. mutans* JH1000. More preferably, the recombinant *S.* mutans strains are generated from *S. mutans* JH1000 variants that produce greater amounts of the bacteriocin relative to the amount produced by *S. mutans* JH1000. A "variant" is a genetically modified bacterium that exhibits a phenotypic alteration relative to the parent strain from which it was derived. The phenotypic alteration can result from any of a variety of genetic lesions, such as an alteration in: 1) the promoter operably linked to the structural gene (e.g., to effect an increase in gene transcription); and/or 2) the structural gene encoding a specific product (e.g., such that the product has enhanced activity). A genetic lesion is an alteration in a wild-type nucleotide sequence that results in a phenotypic alteration in the bacterium.

For example, a "bacteriocin variant" of *S. mutans* JH1000 is a bacterium that has increased bacteriocin activity relative to the *S. mutans* JH1000 parent strain. Preferably, the bacteriocin activity of the *S. mutans* JH1000 variant is increased relative to the bacteriocin activity of the parent *S. mutans* strain, preferably by about 10-fold, preferably about 1.5-fold to 5-fold, more preferably about 2-fold to 4-fold, generally about 3-fold relative to the parent *S. mutans* JH1000 strain. Increased bacteriocin activity of these variants can result from an increased level of bacteriocin production relative to the parent strain, and/or production of a bacteriocin having enhanced antibacterial activity relative to wild-type *S. mutans* bacteriocin.

"Variants" can be generated by a variety of methods well known in the art such as mutagenesis (i.e., exposure of the bacterium to a mutagen), selection of spontaneous mutants, or genetic manipulation using recombinant techniques. Mutagenesis can be accomplished by exposing the bacterium to ultraviolet light, or any of a variety of chemical mutagens, according to methods well known in the art (e.g., ethyl methanesulfonate (EMS), nitrous acid, hydroxylamine, nucleotide analogs (e.g., 5-bromouracil, 2-aminopurine), or intercalating agents (e.g., acridines). Methods for generation of bacterial mutants are well known in the art (see, for example, Sambrook et al., 1989, *Molecular Cloning; A Laboratory Manual*, 2nd Ed., Cold Spring Harbor Laboratory Press, Cold Spring Harbor, N.Y.).

"Spontaneous mutations" are mutations that arise naturally, i.e., without direct genetic manipulation by man, or by exposure to a mutagen. Selection of spontaneous mutants can be accomplished by culturing the strain and selecting the desired variants by, for example, the variant bacterium's production or overproduction of a specific factor, e.g., bacteriocin. Methods for selection of spontaneous mutants are well known in the art (see, for example, Sambrook et al., supra).

Methods for producing variants using recombinant techniques are well known in the art (see, for example, Sambrook et al., 1989, supra). For example, *S. mutans* JH1000 variants having increased bacteriocin activity can be generated by expression of multiple copies of bacteriocin-encoding DNA, and/or mutation of the bacteriocin promoter to provide higher levels of transcription.

Alcohol dehydrogenase genes

Because defects in lactic acid synthesis are lethal for *S. mutans* (Hillman et al., 1994, *Infect. Immun.*, 62:60–64; Hillman et al., 1994, *J. Bacteriol.*, 176:1542–1545), the defect in the recombinant, lactic acid-deficient *S. mutans* strains must be complemented by the production of a recombinant alcohol dehydrogenase (ADH). Production of the recombinant ADH prevents accumulation of metabolites, e.g., pyruvate, that otherwise causes the death of lactic acid-deficient *S. mutans*.

"Production of a recombinant ADH" means that the recombinant *S. mutans* strain expresses a functional ADH enzyme that has been introduced into the *S. mutans* strains using recombinant DNA techniques (i.e., the *S. mutans* has been transformed with DNA encoding an ADH enzyme). "Transformation" means a permanent (i.e., stable) genetic change induced in a cell following incorporation of new DNA (i.e., DNA exogenous to the cell).

The ADH-encoding DNA can be derived from any organism, preferably from a bacterium, more preferably from *Zymomonas mobilis* or *Streptococcus rattus*, even more preferably from *Z. mobilis*. The ADH-encoding DNA can be derived from *S. mutans*, so that introduction of the ADH-encoding DNA, in combination with the native *S. mutans* adh gene, provides for multiples copies of ADH-encoding DNA in the *S. mutans* genome. Alternatively, the recombinant ADH can be generated by introducing a mutation in the regulatory mechanism of the *S. mutans* adh gene (e.g., a mutation in the adh promoter to provide increased transcription of the adh gene). Preferably, the recombinant ADH is alcohol dehydrogenase II of *Z. mobilis*, which has been cloned and sequenced (Genbank Accession No. M15394; Conway et al., 1987, *J. Bacteriol.*, 169:2591–2597, incorporated herein by reference). The amino acid (SEQ ID NO:1) and DNA (SEQ ID NO:2) sequences of *Z. mobilis* alcohol dehydrogenase II are shown in FIG. 1.

Methods for identification, cloning, stable transformation, and expression of DNA fragments encoding a DNA of interest (e.g., ADH) are routine and well known in the art (see, for example, Sambrook et al., 1989, *Molecular Cloning: A Laboratory Manual*, 2nd Ed., Cold Spring Harbor Laboratory Press, Cold Spring Harbor, N.Y.). For example, isolation of DNA encoding ADH can be performed by PCR amplification of the sequence from genomic DNA, or from a preexisting clone of the gene. Expression of recombinant ADH can be accomplished by operably linking the adh structural gene to a promoter that facilitates expression in *S. mutans* (e.g., spaP or the native 1dh promoter).

Production of a functional ADH can be assayed by, for example, using conventional ADH activity assays (e.g., assays for NAD-dependent oxidation of ethanol) that are well known in the art (Neal et al., 1986, *Eur. J. Biochem.*, 154:119–124, incorporated herein by reference).

Generation of lactic acid-deficient *S. mutans*

"Lactic acid deficient" or "deficiency in lactic acid production" means that the *S. mutans* strain produces substantially decreased amounts of lactic acid relative to wild-type *S. mutans*. Preferably, a "lactic acid deficient" recombinant *S. mutans* produces no detectable lactic acid.

Recombinant *S. mutans* strains of the invention are lactic acid deficient as a result of a defect in the lactic acid synthesis pathway. A "defect" is an alteration in the DNA encoding the gene that prevents expression of a functional gene product. "Defects" include alterations that result in inhibition of, or a substantial decrease in, gene transcription and/or translation. "Defects" also include alterations in a structural gene, such that the transcribed and translated gene product is non-functional, or functions at a substantially decreased level relative to the wild-type gene product.

A "defect in the lactic acid synthesis pathway" is a genetic defect that prevents, or substantially decreases, production of lactic acid. Lactic acid synthesis pathway defects can include, for example, genetic lesions in an enzyme that facilitates lactic acid synthesis, and/or a promoter operably linked to a structural gene encoding an enzyme required for lactic acid synthesis. Preferably, the defect in the lactic acid synthesis pathway is due to a defect in the gene encoding lactate dehydrogenase (ldh) (e.g., a defect in the ldh structural gene, and/or a defect in the promoter operably linked to the ldh structural gene). *S. mutans* having a defect in LDH are termed LDH⁻ strains.

The defect in the lactic acid synthesis pathway can be introduced by mutagenesis (i.e., exposure of the bacterium to a mutagen), selection of spontaneous mutants, or genetic manipulation using recombinant techniques. As discussed above, each of these techniques are well known in the art (see, for example, Sambrook et al., supra). Preferably, the lactic acid synthesis pathway defect is introduced using recombinant techniques, e.g., introduction of a defective ldh structural gene into the bacterium and subsequent site-specific recombination to replace the wild-type ldh with the defective ldh. The *S. mutans* ldh gene has been cloned, its nucleotide sequence determined (GenBank accession number M72545), and the recombinant ldh gene expressed in *Escherichia coli* (Duncan et al., 1991, *Infect. Immun.*, 59:3930–3934; Hillman et al., 1990, *Infect. Immun.*, 58:1290–1295, each incorporated herein by reference).

Production of auxotrophic, recombinant *S. mutans* strains

In the event that it becomes desirable to rid the host of the recombinant *S. mutans* colonizing the oral cavity, the infecting recombinant *S. mutans* strain is preferably an auxotroph. An "auxotroph" is a bacterium that requires a source of a specific organic substance(s), in addition to a source of carbon, in order to grow. For example, a "D-alanine auxotroph" is a bacterium that cannot grow without a source of D-alanine. Although auxotrophs can often persist (i.e., survive without growth) for a short period in the absence of the required organic substance, maintenance of auxotrophic colonization requires periodic supplements with that organic substance.

For example, D-alanine auxotrophic bacteria require periodic D-alanine supplements in order to grow and maintain colonization of a niche, such as the oral cavity. Because mammals do not normally produce D-amino acids, and D-alanine is not normally secreted by organisms of the normal flora, D-alanine cannot be acquired by a D-alanine auxotroph from the normal milieu of the host's oral cavity. Thus, use of auxotrophs in the therapeutic method of the invention provide the advantage that oral colonization by the recombinant *S. mutans* can be interrupted by withholding the specific organic supplement, e.g., the D-alanine supplement.

Bacterial auxotrophs can be generated using a variety of techniques well known in the art, such as chemical mutagenesis, selection of spontaneous mutants, and/or recombinant techniques (e.g., transposon mutagenesis, replacement by recombination with a defective or non-functional gene) (see, for example, Sambrook et al., supra). Preferably auxotrophic *S. mutans* strains are generated by either selection of spontaneous mutants, or by recombinant methods (e.g., introduction of a defect in a synthetic pathway for a D-amino acid). Preferably, D-alanine auxotrophic *S. mutans* strains are generated by introduction of a defect in the gene encoding alanine racemase, the enzyme that converts L-alanine to D-alanine. The genes encoding the alanine racemase of several different bacteria have been cloned (*Bacillus stearothermophilus*, Tanizawa et al, (1988) *Biochem*, 27:1311–16; *Bacillus subtilis*, Ferrari et al., *Subtilis;* (1985) *Biotechnol.* (N.Y.) 3:1003–7; *E. coli*, Lobocka, (1994) *J. Bacteriol.* 176:1500–10; *Salmonella typhimurium*, Galakatos et al., (1986) *Biochem.* 23:3255–60; and *Salmonella typhimurium*, Wasserman et al., (1984) *Biochem.* 23:5182–7).

Pharmaceutical compositions containing recombinant *S. mutans* of the invention

A "pharmaceutical composition" is a composition appropriate for oral administration of a recombinant *S. mutans* strain of the invention to a dental caries-susceptible patient. In general, pharmaceutical compositions of the invention are composed of a recombinant *S. mutans* strain and a pharmaceutically acceptable carrier. A "pharmaceutically acceptable carrier" means a vehicle for delivery of a recombinant *S. mutans* strain to the oral cavity of the host, in which the vehicle is compatible with both bacterial cell and host cell viability. Pharmaceutically acceptable carriers suitable for use in the administration of viable recombinant *S. mutans* strains of the invention are well known to those skilled in the art. Selection of the pharmaceutically acceptable carrier will depend upon a variety of factors including the recombinant *S. mutans* strain to be administered, and the formulation used to deliver the recombinant *S. mutans*.

Pharmaceutically acceptable carriers suitable for use with the recombinant *S. mutans* strains of the invention include, but are not limited to, buffered saline solutions (e.g., phosphate-buffered saline), pharmaceutically acceptable culture media (e.g., Luria broth, brain-heart infusion broth (BHI)), or other solutions which maintain the viability of the bacterium. Additionally, such pharmaceutically acceptable carriers may be aqueous or non-aqueous solutions, suspensions, and emulsions. A variety of pharmaceutically acceptable carriers suitable for oral administration of viable or lyophilized bacteria are well known in the art (see, for example, *Remington's Pharmaceutical Sciences*, 18th ed., Gennaro, ed., 1990, Mack Publishing Co., Easton, Pa., incorporated herein by reference; and the pharmaceutical composition LACTINEX™, a commercially available formulation for oral administration of viable Lactobacillus).

The recombinant *S. mutans* strains of the invention can be formulated in any of a variety of compositions suitable for oral administration. For example, the recombinant *S. mutans* strain can be formulated for administration as a lyophil or cell paste prepared from a recombinant *S. mutans* culture, or the recombinant *S. mutans* culture can be directly administered to the oral cavity. The recombinant *S. mutans* strain can also be administered in the form of a mouthwash, toothpaste, floss, chewing gum, or chewable tablet.

The pharmaceutical composition can additionally contain nutrients to maintain the viability of the bacterium in the composition. The pharmaceutical composition can also contain flavoring agents, coloring agents, fragrances, or other compounds which increase the palatability of the composition and/or enhance patient compliance without compromising the effectiveness of the composition. Methods for preparation of formulations for oral administration are well known in the art (see, for example, *Remington's Pharmaceutical Sciences*, 18th ed., supra, incorporated herein by reference).

Compositions for maintenance of auxotrophic recombinant *S. mutans* of the invention Colonization of the oral cavity by recombinant, auxotrophic *S. mutans* strains must be maintained by periodic administration of the organic substance for which the strain is auxotrophic. In the prolonged absence of the organic substance, the auxotrophs will cease growth and the strain can no longer persistently colonize the oral cavity. For example, in the absence of D-alanine, D-alanine auxotrophs undergo lysis due to a weakened cell wall. The use of auxotrophic recombinant *S. mutans* in the therapeutic method of the invention provides a "fail safe" mechanism for eliminating the strain in the event of any undesirable side-effect. However, because the recombinant *S. mutans* strains of the invention are similar to the indigenous *S. mutans* strains that normally colonize the oral cavity, the likelihood of undesirable side-effects is low.

Maintenance of oral cavity colonization by the auxotrophic, recombinant *S. mutans* strains of the invention can be achieved by oral administration of an auxotroph-maintaining amount of the organic substance for which the bacterium is auxotrophic. A "bacterial auxotroph-maintaining amount" is an amount of an organic substance sufficient to maintain viability of the bacterial auxotroph in the oral cavity. For example, where the recombinant *S. mutans* is auxotrophic for D-alanine, a "D-alanine bacterial auxotroph-maintaining amount" is an amount of D-alanine sufficient for survival of the D-alanine auxotrophic strain in the host's oral cavity. In general, a single dose of a D-alanine bacterial auxotroph-maintaining amount of D-alanine contains from about 1 mg to 100 mg, preferably from about 5 mg to 75 mg, more preferably from about 10 mg to 50 mg, even more preferably from about 20 mg to 25 mg of D-alanine. The concentration of D-alanine in the pharmaceutical composition in the form of a solution ranges from about 0.01 mg/ml to 167 mg/ml (the latter being a saturated solution of D-alanine in water at 25° C.), preferably from about 0.1 mg/ml to 50 mg/ml, more preferably from about 1 mg/ml to 25 mg/ml. The concentrations of D-alanine in the pharmaceutical composition can vary according to the carrier used and the saturation point of D-alanine in that specific carrier.

The organic substance required for maintenance of the auxotrophic, recombinant *S. mutans* in the oral cavity can be formulated in a variety of ways. For example, where the recombinant *S. mutans* is auxotrophic for D-alanine, the composition for maintenance of the D-alanine auxotroph can be formulated as a mouthwash, chewing gum, dental floss, toothpaste, chewable tablet, or any other formulation suitable for oral administration to the host's oral cavity. In addition to the organic substance (e.g., D-alanine), the composition can additionally contain flavoring agents, coloring agents, fragrances, or other compounds which increase the palatability of the composition and/or enhance patient compliance without compromising the effectiveness of the organic substance contained in the composition.

The pharmaceutical compositions formulated for oral administration of the recombinant *S. mutans* strains of the invention and, where desired, their maintenance in the oral cavity must be developed within the intrinsic characteristics of the oral cavity and any desirable normal bacterial flora colonizing the oral cavity. Methods for preparation of formulations suitable for oral administration are well known in the art (see, for example, *Remington's Pharmaceutical Sciences*, 18th ed., Gennaro, ed., 1990, Mack Publishing Co., Easton, Pa., incorporated herein by reference).

Administration

The recombinant *S. mutans* strains of the invention can be administered to any dental caries-susceptible host, preferably a host in which *S. mutans* can colonize the oral cavity, preferably a mammalian host (e.g., human, canine, equine, feline, ovine, etc.), more preferably a human host. The recombinant *S. mutans* strains can be administered to the host at any age, e.g., childhood, adolescence, or adulthood.

The recombinant *S. mutans* strains of the invention can be orally administered in a variety of ways. For example, the recombinant *S. mutans* strains may be administered in the form of suspensions, chewable tablets, pills, capsules, sustained release formulas (e.g., an oral implant containing the recombinant *S. mutans* strain) or lyophil powders. The recombinant *S. mutans* strains can also be administered by direct application of a lyophil, culture, or cell paste to the teeth of the patient. Any mode of administration is suitable as long as the therapeutic composition is applied to the oral cavity. Preferably, the recombinant *S. mutans* is administered by applying a bacterial cell suspension directly to the teeth of the patient, e.g., by brushing and flossing.

In general, the amount of recombinant *S. mutans* administered to the patient will be an amount effective for replacement of dental caries-causing *S. mutans* strains in the oral cavity of the host. "An amount effective for replacement of dental caries-causing *S. mutans* strains in the oral cavity of the host" means an amount effective for oral cavity colonization by the recombinant *S. mutans* strain, and elimination of the resident, lactic acid-producing, dental caries-causing *S. mutans* strains (e.g., by competition between the bacteria for nutrients and/or by the production of a bacteriocin by the recombinant *S. mutans* strain). The term "unit dose" when used in reference to a pharmaceutical composition of the present invention refers to physically discrete units suitable as unitary dosage for the subject, each unit containing a predetermined quantity of active material (e.g., viable recombinant *S. mutans*) calculated to produce the desired therapeutic effect in association with the required diluent; i.e., carrier, or vehicle.

Specific dosages can vary widely according to various patient variables including size, weight, age, disease severity (e.g., the tenacity and/or number of lactic acid-producing, dental caries-causing resident *S. mutans*) and responsiveness to therapy (e.g., the susceptibility of the host's oral cavity to colonization). Methods for determining the appropriate route of administration and dosage are generally determined on a case-by-case basis by the attending dentist or other clinician. Such determinations are routine to one of ordinary skill in the art (see, for example, *Remington's Pharmaceutical Sciences*, 8th ed., Gennaro, ed., Mack Publishing Company, Easton, Pa., 1990).

In general, the number of recombinant *S. mutans* administered to the patient will range from about $10^2$ to $10^{15}$ bacteria, preferably from about $10^3$ to $10^{14}$ bacteria, more preferably from about $10^5$ to $10^{12}$ bacteria, normally about $10^{11}$ bacteria. Dosages appropriate for administration can be readily extrapolated from dosages sufficient for Streptococcus spp. colonization of the oral cavity in an animal model, e.g., *S. rattus* colonization of the oral cavity of rats. Appropriate dosages can also be estimated from dosages found appropriate for colonization of the human oral cavity by the bacteriocin-producing strain *S. mutans* JH1000, and variants thereof that express varying levels of bacteriocin activity (Hillman et al., 1987, *J. Dent. Res.*, 66:1092–0194, incorporated herein by reference).

Multiple doses of the recombinant *S. mutans* strains can be administered to achieve oral cavity colonization and replacement of the resident, dental caries-causing *S. mutans* strains of the host. In general, the recombinant *S. mutans* strains of the invention need only be administered to the patient one time. Where the recombinant *S. mutans* strain is an auxotroph, colonization of the strain must be maintained by administration of a composition containing the appropriate organic substance. For example, where the recombinant *S. mutans* strain is a D-alanine auxotroph, D-alanine must be administered for persistent oral cavity colonization. D-alanine, or other appropriate organic substrate, is generally administered at least once a week, preferably at least once a day, more preferably at least twice a day, and can be administered as part of the patient's routine dental care, e.g., as a component of a toothpaste, floss, or mouthwash.

Successful colonization of the host's oral cavity by the recombinant S. mutans strain can be established by culturing the bacteria of the patient's oral cavity, and identifying the recombinant strain by, for example, recombinant ADH production, bacteriocin production, ELISA, growth on selective pH indicator media, or other methods well known in the art for bacterial strain identification.

The following examples are intended to illustrate but not limit the invention. While they are typical of those that might be used, other procedures known to those of ordinary skill in the art may alternatively be used.

EXAMPLES

Example 1

Materials and Methods Bacterial strains, plasmids, and growth conditions

Methods for generating S. mutans strain CH4ts (Chen et al., 1994, J. Bacteriol., 176:1542–1545) and isolating of S. mutans strain NG8 (Lee et al., 1989, Infect. Immun., 57:3306–3313) have been described previously. E coli strain DH5α, used for cloning, is publicly available. Construction of the plasmid pLOI276 (Conway et al., 1987, J. Bacteriol., 169:949–954) containing the cloned Zymomonas mobilis pyruvate decarboxylase (PDC) gene, the plasmid pLOI286 (Conway et al., 1987, J. Bacteriol., 169:2591–2597) containing the cloned Z. mobilis alcohol dehydrogenase II (adh) gene, the pCR2-based plasmid pCR3-8 containing the cloned S. mutans spaP gene (Crowley et al., 1995, J. Dent. Res., 74, abstract no. 1511), and the plasmid pVA981 containing a tetracycline resistance gene derived from S. mutans (Tobian et al., 1984, J. Bacteriol., 160:556–563) have been previously described. Each of the references cited above are hereby incorporated by reference for their respective descriptions of the construction of the indicated plasmids, and the generation or isolation of the recited strains.

Batch and continuous cultures of CH4ts were grown in the defined medium of Carlsson (Carlsson et al., 1970, Caries Res., 4:297–304) supplemented with 0.5% tryptone and 1% glucose. Cells for assay of ADH activity were grown in Todd-Hewitt broth supplemented with 1% glucose. Ampicillin (50 µg/ml), tetracycline (10 µg/ml), and erythromycin (5 µg/ml) were used where appropriate.

Assays of cultures

Samples of batch and continuous cultures were removed at indicated times, and their pH and absorbance at 550 nm determined. Cells were removed by centrifugation at 4° C. and the resulting cell-free liquors were assayed enzymatically (Sigma Chemical Co., St. Louis, Mo.) for glucose, ethanol, and lactic acid and by gas-liquid chromatography (Hillman et al., 1987, Infect. Immun., 55:1399–1402) for acetoin. The pelleted cells were washed once by centrifugation with phosphate-buffered saline (PBS) and assayed chemically (Friedmann et al., 1957, In: S. P. Colowick and N. O. Kaplan (ed), Methods in Enzymology, Academic Press, Inc., New York, p. 414–418) to determine intracellular pyruvate concentrations. The data presented in the figures are the averages of duplicate experiments.

Assay for alcohol dehydrogenase activity

Cells from 200 ml overnight cultures of E. coli and S. mutans strains were recovered by centrifugation at 4° C. and washed twice in 100 mM $KPO_4$ buffer (pH 8.5). The cell pellets were resuspended in 1 ml of buffer and broken by passage through a French press at 15,000 psi. Cell debris was removed by centrifugation at 4° C. for 30 min. The cell-free extracts were kept on ice and assayed for the NAD-dependent oxidation of ethanol according to the methods of Neale et al. (Neal et al., 1986, Eur. J. Biochem., 154:119–124).

Assay for lactate dehydrogenase activity

LDH activity assays were performed as previously described (Hillman et al., 1990, Infect. Immun., 58:1290–1295). Briefly, LDH activity was assayed as the fructose- 1,6-diphosphate (FDP)- and pyruvate-dependent oxidation of NADH measured at 340 nm with a spectrophotometer. The reaction mixture contained 100 µmol potassium phosphate, pH 6.2, 0.2 µmol NADH, 10 µmol sodium pyruvate, and 1–5 µl of the sample to be tested in a final volume of 1 ml. Background levels of activity were measured for 1 min, and then the reaction was initiated by the addition of 20 µmol FDP.

Example 2

Cloning of the Zymomonas mobilis adh structural gene for expression in S. mutans The plasmid pADH contains the Z. mobilis adh open reading frame fused to the regulatory sequences of the S. mutans spaP gene. pADH was constructed by first digesting plasmid pCR3-8 with SacI and DraIII, and then treating the digested DNA with mung bean nuclease to remove the entire spaP gene except for its promoter, ribosome binding site, and 52 bases of the 5' end of the open reading frame. A 4.2 kb fragment of the linearized pCR3-8 plasmid was recovered by agarose gel electrophoresis.

Polymerase chain reaction (PCR) was used to amplify the entire open reading frame of the Z. mobilis adh gene except for its translation start codon (ATG) plus one additional (G) base from the plasmid pLOI286 using forward (5' CTTCTTCAACTTTTTATATTCCTTTCG (SEQ ID NO:3)) and reverse (5' CGGAGGCATTGTTTG (SEQ ID NO:4)) synthetic primers. The amplified fragment was recovered by agarose gel electrophoresis, treated with mung bean nuclease and polynucleotide kinase, and ligated into the pCR3-8 fragment to form the translational fusion with spaP. The resulting plasmid, pADH was used to transform Escherichia ia coli DH5α cells. Transformants of DH5α were selected on LB medium containing ampicillin. The proper size and orientation of the pADH insert were confirmed by restriction enzyme analysis.

In preparation for cloning into S. mutans, pADH was converted to pADH-tet by inserting the 3.5 kb HincII fragment of pVA981 containing a tetracycline resistance gene derived from S. mutans (Tobian et al., 1984, J. Bacteriol., 160:556–563) into the ScaI site of pADH. The pADH-tet construct was used to transform DH5α, and transformants selected on Luria broth (LB) with tetracycline were tested for sensitivity to ampicillin. S. mutans was then transformed with pADH-tet using methods of Perry and Kuramitsu (Perry et al., 1981, Infect. Immun., 32:1295–1297).

Example 3

Effects of glucose concentration upon growth of CH4ts and NG8 in batch cultures

Overnight batch cultures of CH4ts ($1dh^{ts}$) and its parent S. mutans NGS, were grown at 30° C. CH4ts contains a temperature-sensitive mutation of lactate dehydrogenase (LDH). The LDH of CH4ts behaves as wild-type at 30° C., but upon a culture temperature shift to 42° C., the heat-labile LDH is inactive. This strain thus allows experiments to determine the role of LDH in the lethality of LDH-mutants of S. mutans. Washed cells were diluted 1:1000 in fresh medium with and without glucose and incubated in a 42° C. water bath. At time points indicated in FIG. 2 (Panel A), viable cell counts were determined by spreading samples on brain heart infusion (BHI) plates and incubating the plates at 30° C. The results show that in the absence of glucose (dashed lines), CH4ts (open triangles) and NG8 (open circles) behaved identically: growth ceased after 3 hrs and was followed by slow cell death (half life=23.5 hrs). However, unlike its parent (open squares), CH4ts (open circles) stopped growing within 3 hrs of being placed in the presence of glucose (solid lines) and underwent accelerated cell death (half life=12.1 hrs). This difference correlated temporally with the accumulation of high intracellular concentrations of pyruvate in the mutant (FIG. 2, Panel B).

Example 4

Figure 3:
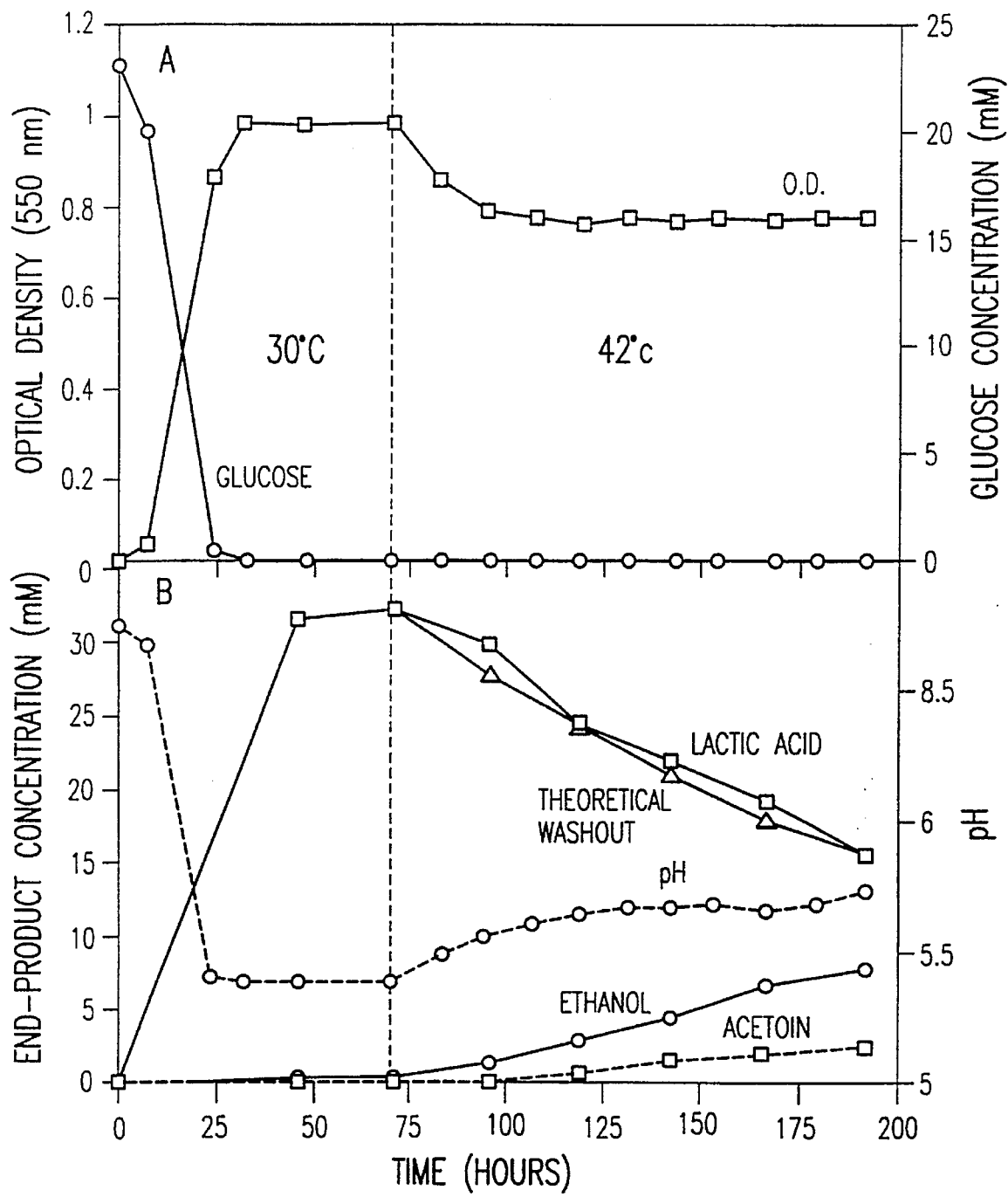
FIG. 3 shows the effects of glucose concentration and temperature upon continuous culture of *Streptococcus mutans* strain CH4ts at a 10% dilution rate. Panel A Symbols: —□—, optical density; —o—, glucose concentration; Panel B Symbols: --o--, pH; —□—, lactic acid concentration; —Δ—, theoretical washout; —o—, ethanol concentration; —□—, acetoin concentration.

Effect of glucose and temperature upon growth and end-product concentration in CH4ts and NG8 in continuous culture CH4ts was grown to saturation at 30° C. in the reaction vessel of a chemostat. Medium inflow providing a dilution rate of 0.1 $hr^{-1}$ was maintained for 72 hrs before the temperature of the culture was shifted to 42° C. Within 3 hours, the cell density began to decline at a rate equivalent to the theoretical washout rate, indicating a cessation of cell growth (FIG. 3). This correlated with an increase in the glucose concentration observed in the reaction vessel.

Figure 4:
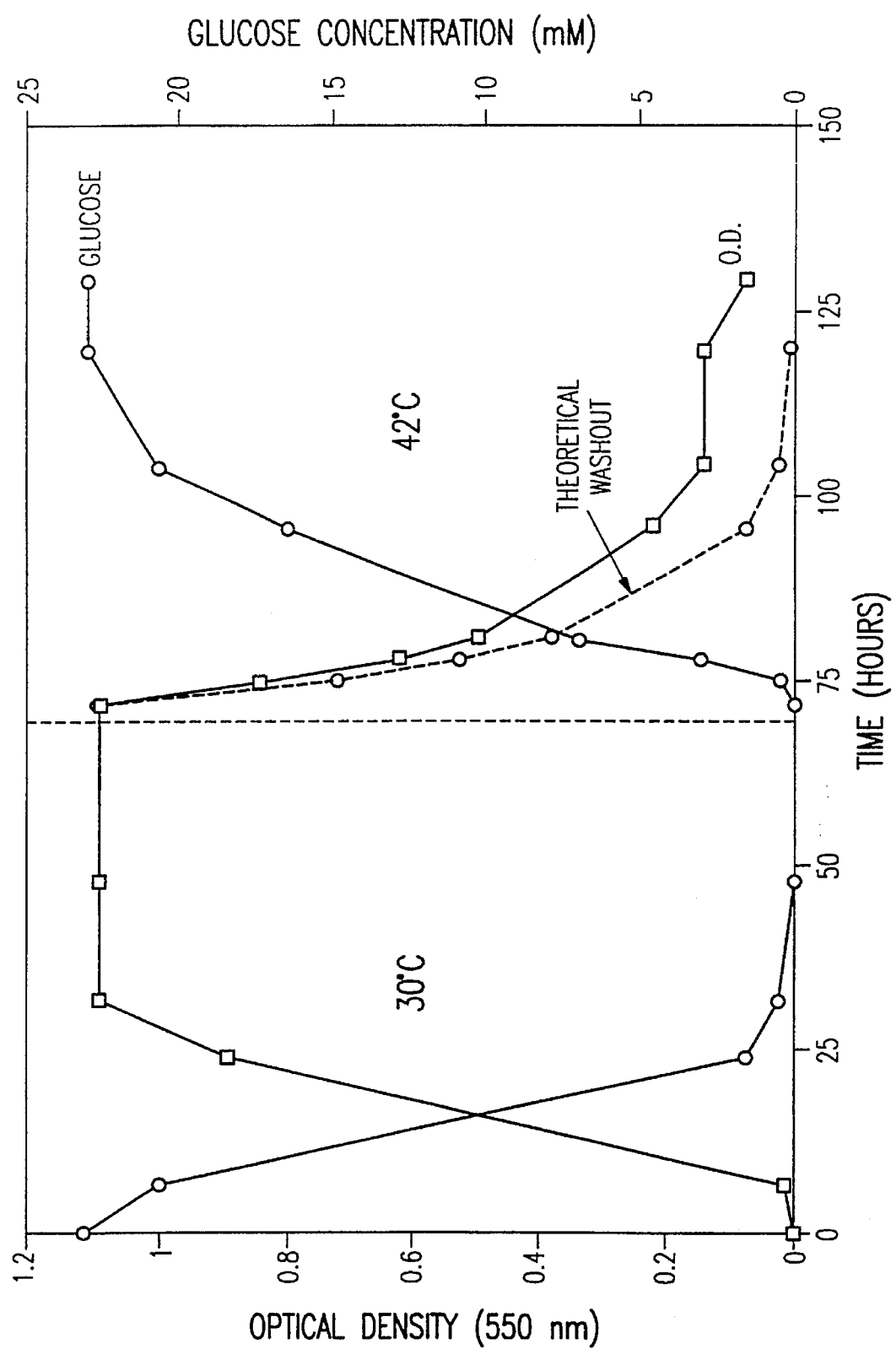
FIG. 4 shows the effects of glucose concentration and temperature upon continuous culture of *Streptococcus mutans* strain CH4ts at a 0.6% dilution rate. Symbols: —□—, optical density; —o—, glucose; --o--, theoretical washout.

When the continuous culture experiment was repeated using a dilution rate of 0.006 $hr^{-1}$ stable growth of CH4ts was achieved when the temperature was shifted to 42° C. (FIG. 4). Immediately following the temperature shift, lactic acid concentrations declined in agreement with the predicted washout rate. Cessation of lactate production was accompanied by initiation of ethanol and acetoin production, resulting in a gradual increase in the pH of the continuous culture. Glucose concentrations remained undetectable throughout the experiment.

These data show that stable growth of CH4ts at 42° C. can be achieved in continuous culture under glucose-limiting conditions. Under glucose-limiting conditions, CH4ts behaved like chemically-derived LDH-deficient mutants of *S. rattus* (Hillman et al., 1987, *Infect. Immun.*, 55:1399–1402) with respect to increased ethanol and acetoin production in place of lactic acid production. These results accord with fermentation and enzymology studies indicating that *S. mutans* has regulated, alternate pathways for pyruvate metabolism. Under appropriate conditions of cultivation, wild-type *S. mutans* produces substantial amounts of formate, acetate, ethanol and acetoin (Yamada et al., 1975, *J. Bacteriol.*, 124:55–61; Hillman et al., 1987, *Infect. Immun.*, 55:1399–1402) in addition to lactate. However, these alternate pathways are apparently insufficient to compensate for the absence of LDH activity.

Example 5

Production of ADH rescues LDH⁻ lethality in *S. mutans*

*E. coli* strain DH5α transformed with pADH, which contains the *Z. mobilis* adh open reading frame fused to the *S. mutans* spaP regulatory sequences, expressed the cloned ADH activity (specific activity 6.95 μmol/min/mg protein). This result agreed with previously published data indicating that the spaP promotor and ribosome binding site (rbs) are active in *E. coli* (Lee et al., 1988, *Infect. Immun.*, 56:2114–2119). The level of ADH activity was approximately 17% of that found in DH5α transformed with pLOI286 (specific activity 41.8 μmol/min/mg protein), which has the original cloned adh gene and regulatory sequences from *Z. mobilis*. Interruption of the ampicillin resistance gene on the pCR2 backbone by insertion of the tetracycline resistance gene from pVA981 (pADH-tet) did not affect the level of ADH activity.

One microgram of pADH-tet was used to transform CH4ts. Campbell type recombination installed the spaP::adh fusion into the chromosome of CH4ts. The site of insertion was not identified, but likely is at a region of homology provided by either spaP or the endogenous adh gene. Transformed CH4ts were selected for growth at 42° C. on medium containing tetracycline. From several hundred clones which arose, one purified isolate called CH4ts::adh contained substantially more ADH activity (specific activity, 60.43 μmol/min/mg protein) than its wild-type grandparent NG8 (specific activity, <1.0 μmol/min/mg protein).

CH4ts::adh and NG8 were grown at 42° C. for 48 hrs in Todd-Hewitt broth supplemented with 2% glucose. Cell-free culture liquors of CH4ts::adh had a significantly higher pH (4.7) and ethanol content (21.60 mM) than did culture liquors of NG8 (4.0 and <1 mM). Identical results were obtained when higher (5, 10 or 20%) concentrations of glucose were used.

The growth of CH4ts::adh at 42° C. in defined medium supplemented with 0.5% tryptone and various carbon sources at 1% was compared to NG8 (Table 1).

TABLE 1

| | Growth properties of wild-type and ADH-complemented LDH-deficient *S. mutans* | | | | | | | |
|---|---|---|---|---|---|---|---|---|
| | Doubling Time (hr) | | Yield (O.D.$_{550}$) | | Lactate (mM) | | Ethanol (mM) | |
| Carbon Source | NG8 | CH4ts::ADH | NG8 | CH4ts::ADH | NG8 | CH4ts::ADH | NG8 | CH4ts::ADH |
| glucose | 2.1 | 2.0 | 0.94 | 1.08 | 20.1 | 0 | 1.4 | 21.2 |
| galactose | 4.8 | 2.4 | 0.68 | 0.99 | 19.3 | 0 | 1.3 | 18.9 |
| lactose | 1.9 | 2.2 | 0.95 | 1.03 | 19.9 | 0 | 0.1 | 19.9 |
| mannitol | 4.5 | 2.0 | 0.36 | 0.94 | 5.9 | 0 | 4.5 | 26.2 |
| sorbitol | 8.0 | 3.0 | 0.35 | 0.97 | 3.8 | 0 | 3.6 | 26.1 |
| sucrose | 2.6 | 3.4 | 0.78 | 0.74 | 20.4 | 0 | 0 | 19.7 |

Results are the average of two independent experiments.
Other fermentation end-products besides lactate and ethanol were not determined.

The rates and cell yields were comparable when glucose, lactose or sucrose served as the carbon source. CH4ts::adh had substantially shorter doubling times and higher yields than NG8 when galactose, sorbitol or mannitol served as the carbon source. No lactic acid was detected in culture liquors of CH4ts::adh grown on any of the carbon sources, and ethanol was present in much greater amounts than was found in culture liquors of NG8.

These data show that the recombinant *S. mutans* strain CH4ts::adh exhibited substantially higher levels of ADH activity than NG8 wild-type control strain under identical conditions of growth. Moreover, transformants of CH4ts grew at the non-permissive temperature, indicating that the cloned ADH activity circumvented the metabolic blockade caused by LDH-deficiency.

These data further show that the growth rates and growth yields of CH4ts::adh and NG8 are similar when glucose, lactose or sucrose served as the sole carbon source, and growth yields were also comparable. However, NG8 grew poorly on both mannitol and sorbitol under aerobic conditions, but CH4ts::adh grew well. This result indicates that the cloned ADH activity provided sufficient ethanol production to serve as a suitable sink for excess electrons generated during polyol metabolism. NG8 also grew poorly on galactose. It is not clear why CH4ts::adh should grow better than NG8 on this carbon source which is metabolized via the tagatose 6-phosphate pathway in *S. mutans* (Hamilton et al., 1979, *J. Bacteriol.*, 140:1102–1104), particularly since their growth on lactose was comparable.

Example 6

Production of pyruvate decarboxylase does not rescue LDH- lethality in *S. mutans*

A study similar to that described in Examples 2–5 was performed to determine if a defect in LDH could be rescued by production of a pyruvate decarboxylase. The pyruvate decarboxylase (pdc) gene from *Z. mobilis* (Conway et al., 1987, *J. Bacteriol.*, 169:949–954) was fused to spaP and introduced into CH4ts on a suicide vector as described for the *Z. mobilis* adh gene. Tetracycline-resistant, PDC-expressing transformants were isolated and tested for growth at the non-permissive 42° C. temperature as described above. LDH⁻ *S. mutans* expressing the cloned PDC activity were did not grow at the non-permissive temperature. These results indicate that the lethality of the LDH⁻ defect in *S. mutans* cannot be rescued by production of PDC. Further, these data indicate that the concentration of ADH was not saturating in the metabolism of pyruvate in LDH-deficient mutants of *S. mutans*.

Example 7

Isolation of JH1000 and JH1000 variants producing increased levels of bacteriocin activity Isolation of the *S. mutans* JH1000 has been described (Hillman et al., 1984, *Infect. Immun.*, 44:141–144). Briefly, JH1000 was identified from fresh isolates of mutans streptococci obtained from 115 subjects on mitis salivarius agar containing bacitracin. JH1000 inhibited the growth of all of the other *S. mutans* strains, as well as a large number and variety of laboratory strains in a deferred antagonism assay. Evidence indicates (Hillman et al., 1984, *Infect. Immun.*, 44:141–144) that JH1000 produces a small (less than 1,000 Da), stable antibiotic-like, bacteriocin-like compound which is currently being characterized. This compound is termed *S. mutans* bacteriocin. Microbiological and serological assays confirmed that JH1000 is a representative of the *S. mutans* species. Variants of bacteriocin-susceptible strains, either naturally-occurring or generated by chemical mutagenesis, that are resistant to the killing properties of bacteriocin have not been identified. This result indicates that, unlike most antibiotics, the risk of superinfection by resistant, wild-type (disease-causing) strains is minimal.

The JH1000 strain was subjected to chemical mutagenesis using ethyl methanesulfonate (EMS) according to methods well known in the art (Hillman 1978, *Infect. Immun.*, 21:206–212). JH1005 is an exemplary EMS-induced variant of JH1000. Variants producing increased levels of bacteriocin were identified by growing a broth culture of the strain to be tested for 8 hrs or more. The culture was centrifuged to remove the bacterial cells, and 20 µl samples of the culture supernatant were serially diluted in wells of a microtiter plate. 100 µl of Top agar containing a target strain (usually *S. rattus* BHT-2, Str$^R$) and 1 mg/ml streptomycin was added to each well. After incubation overnight, the lowest dilution that prevented growth of the indicator strain was determined.

Using this overlay method, EMS-derived (JH1005) and spontaneous (JH1140) variants of JH1000 were found which produce approximately 3-fold elevated levels of the bacteriocin-like activity. JH1000, as well as the JH1000 variants, produce lactic acid, and thus are not suitable for replacement therapies for the prevention and/or treatment of dental caries.

Example 8

Colonization of the human oral cavity by *S. mutans* JH1000 variants

Colonization of the oral cavity of rodents and humans by JH1000 variants having increased bacteriocin activity has been described (Hillman et al., 1987, *J. Dent. Res.*, 66:1092–1094). Briefly, JH1000 or JH1000 variants were applied to the teeth of human volunteers using an infection regimen which involved a standard dental prophylaxis, followed by brushing and flossing a cell suspension containing about $10^{11}$ JH1000 bacteria or JH1000 variant bacteria.

The level of bacteriocin activity and the ability to colonize the oral cavity were strongly correlated. Over a 1 year period after infection with the JH1005 strain, the indigenous mutans streptococci were gradually replaced by JH1005. In addition, the total numbers of mutans streptococci were significantly decreased in two of the three subjects tested.

Example 9

Generation of recombinant mutants of *S. mutans* using transposon mutagenesis. *S. mutans* strain Plasmid pTV1-OK is a repA(ts) derivative of the *Lactococcus lactis* plasmid pWV01 (Leenhouts et al., 1991, *Plasmid*, 26:55–66) for conditional replication in both *S. mutans* and *E. coli*. It possesses a kanamycin resistance gene on the plasmid backbone that is expressed in both *E. coli* and *S. mutans* and the transposon Tn917 which confers erythromycin resistance in *S. mutans*.

The pTV1-OK plasmid was introduced into *S. mutans* strain JH1005, and transformed cells were selected at 28° C. on BHI agar containing kanamycin. Transformation of JH1005 with 1 mg of pTV1-OK DNA yielded four kanamycin resistant transformants, which is in agreement with transformation frequencies from earlier experiments (Hillman et al., 1994, *Infect. Immun.*, 62:60–64). Independent pools of Tn917 insertions into host chromosomal DNA were generated by temperature shift (45° C.) as described by Camilli et al. (1990, *J. Bacteriol*, 172:3738–3744). Briefly, saturated cultures grown in the presence of kanamycin at the permissive temperature (28° C.) were subcultured 1/50 or 1/100. Following a shift to 45° C. and overnight incubation, insertions of Tn917 into the host chromosome were isolated by plating samples on BHI agar containing selective concentrations of erythromycin. It was found that $10^5$ of $10^9$ total colony-forming units retained their resistance to this antibiotic. Ninety of 100 randomly chosen erythromycin-resistant colonies were shown by replica patching to be sensitive to kanamycin. This finding indicated that 90% of the erythromycin-resistant clones were the result of the coincident loss of pTV1-OK and the transposition of Tn917 into the JH1005 chromosome. Southern blot analysis of randomly selected erythromycin-resistant mutants suggested that Tn917 transposition was random and resulted in single chromosomal insertions. Southern blot analysis also indicated that the 10% erythromycin-resistant/kanamycin-resistant clones were the result of replicon fusions which installed the entire pTV1-OK plasmid in the JH1005 chromosome.

Independent pools of kanamycin-sensitive clones were screened for bacteriocin production, sensitivity to 1% glycine, acid sensitivity, and inability to grow anaerobically on mannitol or in the absence of D-alanine supplementation. Mutants in each category were isolated at frequencies ranging from 1 to $2 \times 10^{-3}$.

Southern blot analysis of two bacteriocin deficient mutants indicated the existence of at least two unlinked genes involved in bacteriocin production and at least three unlinked genetic loci involved in acid sensitivity. Upon introduction of the Tn917-induced acid sensitive alleles isolated in JH1005 into NG8 via natural transformation, the transposon (encoding erythromycin resistance) was co-inherited with the mutant phenotypes at high frequencies. This linkage indicates that the lesion induced by Tn917 was responsible for the mutant phenotypes. Pools of Tn917 mutants have also been obtained in the naturally transformable strain NG8 with similar transposition frequencies and efficiencies of plasmid loss after temperature shift.

One gene involved in bacteriocin production has been cloned in *E. coli* using a marker rescue technique. The chromosomal DNA from the mutant was digested to completion with EcoRI (which does not cut within Tn917) and ligated into the EcoRI site in the multiple cloning sequence of pUC19. The library was transformed into MC1061 with selection for ampicillin resistance, and colonies which arose were replicated onto medium with erythromycin. Two clones which arose were shown to contain plasmid DNA which reacted in dot blot analysis with a Tn917 probe. These plasmids are currently being sequenced using primers which read outward from the erythromycin-proximal and erythromycin-distal ends of Tn917.

This is the successful use Tn917 mutagenesis in *S. mutans* and oral streptococci. Previous failures using constructs such as pTV1 or pLTV3 (Youngman, 1987, In: *Plasmids: A Practical Approach,* Hardy, ed., IRL Press, Oxford, pgs. 79–103; Camilli et al., 1990, *J. Bacteriol.,* 172:3738–3744) were attributed to the inability of the plasmid backbones to replicate in *S. mutans.* Using the replicative functions of the Lactococcus replicon pWV01Ts, pTV1-OK was found to be stably maintained at the permissive temperature in *S. mutans,* thereby providing sufficient opportunity for Tn917 transposition to occur at the non-permissive temperature. Thus, the method described above can be used to generate auxotrophic *S. mutans* strains, as well as other *S. mutans*-derived strains having desirable phenotypes, for use in the present invention.

Example 10

Construction of an LDH⁻, ADH⁺, bacteriocin-producing *S. mutans* Strain

The 1dh gene of JH1000 has been cloned and sequenced (Hillman et al., 1990, *Infect. Immun.,* 58:1290–1295; Duncan et al., 1991, *Infect. Immun.,* 59:3930–3934). Briefly, the JH1000 1dh gene was cloned into *Escherichia coli* strain MC1061 using pBR322 as the vector. One clone, p10-5, containing the 1dh gene was identified by hybridization with an oligonucleotide probe deduced from the amino-terminal sequence of the LDH protein purified from JH1000 (Hillman et al., 1990, *Infect. Immun.,* 58:1290–1295). These results were verified by demonstrating JH1000 LDH activity in crude cell-free extracts of the p10-5/MC1061 transformant. The nucleotide sequence of the cloned 1dh was determined and its regulatory signals and open reading frame deduced. The sequence of the JH1000 1dh gene is available from GenBank, accession number M72545 (description LDH SM).

The cloned 1dh gene is inactivated by digesting the p10-5 construct with the restriction enzyme HpaI. This results in the removal of 510 bases from the 1dh open reading frame, thus permanently inactivating the gene. The appropriate sized DNA fragment from this digestion is recovered by agarose gel electrophoresis, treated with mung bean nuclease to produce blunt ends, and dephosphorylated by reaction with calf intestinal phosphatase.

The entire open reading frame of the *Z. mobilis* adh gene (except for substitution of the first three bases with a guanidine residue and the addition of a translational and transcriptional codon at the end of the open reading frame) is amplified by PCR. After gel purification, this fragment is treated with mung bean nuclease to produce blunt ends, and phosphorylated by reaction with polynucleotide kinase. This product and the p10-5 product described above are ligated and transformed into *E. coli* DH5α with selection for ampicillin resistance. Permeabilized cells of purified clones are then screened for ADH activity as described above. Plasmids from ADH positive clones are then purified and checked by restriction mapping to confirm the genetic construct.

One such genetic construct is further modified by elimination of the ampicillin resistance gene on the pBR322 backbone, and replacement with the tetracycline resistance gene from pVA981. This construct is used to transform JH1140, transformants are selected on tetracycline-containing medium. Heterodiploid transformants which arise are purified, grown overnight in Todd-Hewitt broth, and appropriate dilutions spread on glucose tetrazolium-medium. After 3 days incubation in candle jars, red colonies which arise, indicating deletion of LDH (or indicating reduced acid production), are isolated and purified as putative LDH-deficient mutants.

The phenotype and genotype of the transformants is confirmed by assaying 2 day old broth cultures for lactic acid and ethanol, by Southern blot analysis, and by spectrophotometric assays of cell-free extracts for LDH activity as described above. The lactic acid production in these strains is expected to be undetectable, while the ethanol content of the medium is expected to be about 25 mM in broth containing 1% or more glucose. The LDH activity of these transformants is expected to be undetectable.

The transformant strains are further characterizations by examining the growth of the parent and transformant on various carbon sources, with and without oxygen. The transformant is expected to grow as well or better than the parent strain in terms of generation time and cell yield. The parent and transformant strains are also grown in chemostat cultures in order to accurately assess fermentation end-products under different conditions of growth. The transformant strain is expected to produce no detectable lactic acid under all cultivation conditions, and to make significant acetoin only during aerobic incubation.

The cariogenic potential of the transformant is also determined in a rat model of dental caries using conventional and/or germfree rats. The transformant is expected to be virtually non-cariogenic, while the parent strain should produce a high incidence and severity of carious lesions. Plaque production and bacteriocin production by the transformant and parent strain are also assayed.

Where the transformant strain at least minimally satisfies the expectations described above (i.e., is deficient in lactic acid production, and is non-cariogenic), the transformant is a recombinant *S. mutans* strain suitable for use in the prevention or treatment of dental caries.

The following bacterial strains have been deposited on or before Jun. 7, 1995, with the American Type Culture Collection, 1301 Parklawn Drive, Rockville, Md., USA (ATCC).

| Deposit | ATCC Accession No. |
|---|---|
| JH1000 | ACCESSION NO. 55677 |
| JH1140 | ACCESSION NO. 55676 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The bacteria will be made available by ATCC under the terms of the Budapest Treaty and Applicant assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the culture deposit should die or be lost or destroyed when cultivated under suitable conditions, it will be promptly replaced on notification with a viable specimen of the same culture. Availability of the deposited strain is not to be construed as a license to practice the invention in the contravention of the rights granted under the authority of any government in accordance with its patent laws.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1747 base pairs
( B ) TYPE: nucleic acid
( C ) STRANDEDNESS: double
( D ) TOPOLOGY: linear ( i i ) MOLECULE TYPE: DNA ( i x ) FEATURE:
( A ) NAME/KEY: CDS
( B ) LOCATION: 432..1747

( x i ) SEQUENCE DESCRIPTION: SEQ ID NO:1:

```
AAAGGCAAAA  TCGGTAACCA  CATCTCAATT  ATTAAACAAT  ACTTCATAAT  AAAAAGACAA        60

CTTTTTCATA  ATTTGCATAA  GTCTTGATGT  AAAAAATACA  TATTTAGAAA  GAACAAGCAG       120

CCTTGCTCAT  CACCGCTGTC  GCGAGTAGAA  AAATCTCGGC  TTTCAGAAAA  AGAGGCCGCT       180

TCGTTAAACA  GACTATAAAT  GTGCTGGAAT  AAAGCGAACC  CCTTGATCTG  ATAAAACTGA       240

TAGACATATT  GCTTTTGCGC  TGCCCGATTG  CTGAAAATGC  GTAAAAGGTG  ATTTTACTCG       300

TTTTCAGGAA  AAACTTTGAG  AAAACGTCTC  GAAAACGGGA  TTAAAACGCA  AAAACAATAG       360

AAAGCGATTT  CGCGAAAATG  GTTGTTTTCG  GGTTGTTGCT  TTAAACTAGT  ATGTAGGGTG       420

AGGTTATAGC  T ATG GCT  TCT TCA ACT  TTT TAT ATT  CCT TTC GTC  AAC GAA         470
            Met Ala    Ser Ser Thr  Phe Tyr Ile  Pro Phe Val  Asn Glu
              1                       5                         10

ATG GGC GAA GGT TCG CTT GAA AAA GCA ATC AAG GAT CTT AAC GGC AGC              518
Met Gly Glu Gly Ser Leu Glu Lys Ala Ile Lys Asp Leu Asn Gly Ser
     15                  20                  25

GGC TTT AAA AAT GCG CTG ATC GTT TCT GAT GCT TTC ATG AAC AAA TCC              566
Gly Phe Lys Asn Ala Leu Ile Val Ser Asp Ala Phe Met Asn Lys Ser
 30                  35                  40                  45

GGT GTT GTG AAG CAG GTT GCT GAC CTG TTG AAA GCA CAG GGT ATT AAT              614
Gly Val Val Lys Gln Val Ala Asp Leu Leu Lys Ala Gln Gly Ile Asn
```

```
                      50                          55                          60
TCT GCT GTT TAT GAT GGC GTT ATG CCG AAC CCG ACT GTT ACC GCA GTT      662
Ser Ala Val Tyr Asp Gly Val Met Pro Asn Pro Thr Val Thr Ala Val
             65                      70                  75

CTG GAA GGC CTT AAG ATC CTG AAG GAT AAC AAT TCA GAC TTC GTC ATC      710
Leu Glu Gly Leu Lys Ile Leu Lys Asp Asn Asn Ser Asp Phe Val Ile
         80                      85                      90

TCC CTC GGT GGT GGT TCT CCC CAT GAC TGC GCC AAA GCC ATC GCT CTG      758
Ser Leu Gly Gly Gly Ser Pro His Asp Cys Ala Lys Ala Ile Ala Leu
     95                     100                     105

GTC GCA ACC AAT GGT GGT GAA GTC AAA GAC TAC GAA GGT ATC GAC AAA      806
Val Ala Thr Asn Gly Gly Glu Val Lys Asp Tyr Glu Gly Ile Asp Lys
110                     115                     120                 125

TCT AAG AAA CCT GCC CTG CCT TTG ATG TCA ATC AAC ACG ACG GCT GGT      854
Ser Lys Lys Pro Ala Leu Pro Leu Met Ser Ile Asn Thr Thr Ala Gly
                130                     135                     140

ACG GCT TCT GAA ATG ACG CGT TTC TGC ATC ATC ACT GAT GAA GTC CGT      902
Thr Ala Ser Glu Met Thr Arg Phe Cys Ile Ile Thr Asp Glu Val Arg
            145                     150                     155

CAC GTT AAG ATG GCC ATT GTT GAC CGT CAC GTT ACC CCG ATG GTT TCC      950
His Val Lys Met Ala Ile Val Asp Arg His Val Thr Pro Met Val Ser
        160                     165                     170

GTC AAC GAT CCT CTG TTG ATG GTT GGT ATG CCA AAA GGC CTG ACC GCC      998
Val Asn Asp Pro Leu Leu Met Val Gly Met Pro Lys Gly Leu Thr Ala
175                     180                     185

GCC ACC GGT ATG GAT GCT CTG ACC CAC GCA TTT GAA GCT TAT TCT TCA     1046
Ala Thr Gly Met Asp Ala Leu Thr His Ala Phe Glu Ala Tyr Ser Ser
190                     195                     200                 205

ACG GCA GCT ACT CCG ATC ACC GAT GCT TGC GCC TTG AAG GCT GCG TCC     1094
Thr Ala Ala Thr Pro Ile Thr Asp Ala Cys Ala Leu Lys Ala Ala Ser
                210                     215                     220

ATG ATC GCT AAG AAT CTG AAG ACC GCT TGC GAC AAC GGT AAG GAT ATG     1142
Met Ile Ala Lys Asn Leu Lys Thr Ala Cys Asp Asn Gly Lys Asp Met
            225                     230                     235

CCA GCT CGT GAA GCT ATG GCT TAT GCC CAA TTC CTC GCT GGT ATG GCC     1190
Pro Ala Arg Glu Ala Met Ala Tyr Ala Gln Phe Leu Ala Gly Met Ala
        240                     245                     250

TTC AAC AAC GCT TCG CTT GGT TAT GTC CAT GCT ATG GCT CAC CAG TTG     1238
Phe Asn Asn Ala Ser Leu Gly Tyr Val His Ala Met Ala His Gln Leu
255                     260                     265

GGC GGC TAC TAC AAC CTG CCG CAT GGT GTC TGC AAC GCT GTT CTG CTT     1286
Gly Gly Tyr Tyr Asn Leu Pro His Gly Val Cys Asn Ala Val Leu Leu
270                     275                     280                 285

CCG CAT GTT CTG GCT TAT AAC GCC TCT GTC GTT GCT GGT CGT CTG AAA     1334
Pro His Val Leu Ala Tyr Asn Ala Ser Val Val Ala Gly Arg Leu Lys
                290                     295                     300

GAC GTT GGT GTT GCT ATG GGT CTC GAT ATC GCC AAT CTC GGT GAT AAA     1382
Asp Val Gly Val Ala Met Gly Leu Asp Ile Ala Asn Leu Gly Asp Lys
            305                     310                     315

GAA GGC GCA GAA GCC ACC ATT CAG GCT GTT CGC GAT CTG GCT GCT TCC     1430
Glu Gly Ala Glu Ala Thr Ile Gln Ala Val Arg Asp Leu Ala Ala Ser
        320                     325                     330

ATT GGT ATT CCA GCA AAT CTG ACC GAG CTG GGT GCT AAG AAA GAA GAT     1478
Ile Gly Ile Pro Ala Asn Leu Thr Glu Leu Gly Ala Lys Lys Glu Asp
335                     340                     345

GTG CCG CTT CTT GCT GAC CAC GCT CTG AAA GAT GCT TGT GCT CTG ACC     1526
Val Pro Leu Leu Ala Asp His Ala Leu Lys Asp Ala Cys Ala Leu Thr
350                     355                     360                 365

AAC CCG CGT CAG GGT GAT CAG AAA GAA GTT GAA GAA CTC TTC CTG AGC     1574
Asn Pro Arg Gln Gly Asp Gln Lys Glu Val Glu Glu Leu Phe Leu Ser
```

|  | 370 |  |  |  |  |  | 375 |  |  |  |  |  | 380 |  |  |  |
|---|---|---|---|---|---|---|---|---|---|---|---|---|---|---|---|---|
| GCT | TTC | TAA | TTT | CAA | AAC | AGG | AAA | ACG | GTT | TTC | CGT | CCT | GTC | TTG | ATT | 1622 |
| Ala | Phe |  |  |  |  |  |  |  |  |  |  |  |  |  |  |  |
| TTC | AAG | CAA | ACA | ATG | CCT | CCG | ATT | TCT | AAT | CGG | AGG | CAT | TTG | TTT | TTG | 1670 |
| TTT | ATT | GCA | AAA | ACA | AAA | AAT | ATT | GTT | ACA | AAT | TTT | TAC | AGG | CTA | TTA | 1718 |
| AGC | CTA | CCG | TCA | TAA | ATA | ATT | TGC | CAT | TT |  |  |  |  |  |  | 1747 |

( 2 ) INFORMATION FOR SEQ ID NO:2:

( i ) SEQUENCE CHARACTERISTICS:
        ( A ) LENGTH: 383 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Ser | Ser | Thr | Phe | Tyr | Ile | Pro | Phe | Val | Asn | Glu | Met | Gly | Glu |
|---|---|---|---|---|---|---|---|---|---|---|---|---|---|---|---|
| 1 |  |  |  | 5 |  |  |  |  | 10 |  |  |  |  | 15 |  |
| Gly | Ser | Leu | Glu | Lys | Ala | Ile | Lys | Asp | Leu | Asn | Gly | Ser | Gly | Phe | Lys |
|  |  |  | 20 |  |  |  |  | 25 |  |  |  |  | 30 |  |  |
| Asn | Ala | Leu | Ile | Val | Ser | Asp | Ala | Phe | Met | Asn | Lys | Ser | Gly | Val | Val |
|  |  | 35 |  |  |  |  | 40 |  |  |  |  | 45 |  |  |  |
| Lys | Gln | Val | Ala | Asp | Leu | Leu | Lys | Ala | Gln | Gly | Ile | Asn | Ser | Ala | Val |
|  | 50 |  |  |  |  | 55 |  |  |  |  | 60 |  |  |  |  |
| Tyr | Asp | Gly | Val | Met | Pro | Asn | Pro | Thr | Val | Thr | Ala | Val | Leu | Glu | Gly |
| 65 |  |  |  |  | 70 |  |  |  |  | 75 |  |  |  |  | 80 |
| Leu | Lys | Ile | Leu | Lys | Asp | Asn | Asn | Ser | Asp | Phe | Val | Ile | Ser | Leu | Gly |
|  |  |  |  | 85 |  |  |  |  | 90 |  |  |  |  | 95 |  |
| Gly | Gly | Ser | Pro | His | Asp | Cys | Ala | Lys | Ala | Ile | Ala | Leu | Val | Ala | Thr |
|  |  |  | 100 |  |  |  |  | 105 |  |  |  |  | 110 |  |  |
| Asn | Gly | Gly | Glu | Val | Lys | Asp | Tyr | Glu | Gly | Ile | Asp | Lys | Ser | Lys | Lys |
|  |  | 115 |  |  |  |  | 120 |  |  |  |  | 125 |  |  |  |
| Pro | Ala | Leu | Pro | Leu | Met | Ser | Ile | Asn | Thr | Thr | Ala | Gly | Thr | Ala | Ser |
|  | 130 |  |  |  |  | 135 |  |  |  |  | 140 |  |  |  |  |
| Glu | Met | Thr | Arg | Phe | Cys | Ile | Ile | Thr | Asp | Glu | Val | Arg | His | Val | Lys |
| 145 |  |  |  |  | 150 |  |  |  |  | 155 |  |  |  |  | 160 |
| Met | Ala | Ile | Val | Asp | Arg | His | Val | Thr | Pro | Met | Val | Ser | Val | Asn | Asp |
|  |  |  |  | 165 |  |  |  |  | 170 |  |  |  |  | 175 |  |
| Pro | Leu | Leu | Met | Val | Gly | Met | Pro | Lys | Gly | Leu | Thr | Ala | Ala | Thr | Gly |
|  |  |  | 180 |  |  |  |  | 185 |  |  |  |  | 190 |  |  |
| Met | Asp | Ala | Leu | Thr | His | Ala | Phe | Glu | Ala | Tyr | Ser | Ser | Thr | Ala | Ala |
|  |  | 195 |  |  |  |  | 200 |  |  |  |  | 205 |  |  |  |
| Thr | Pro | Ile | Thr | Asp | Ala | Cys | Ala | Leu | Lys | Ala | Ala | Ser | Met | Ile | Ala |
|  | 210 |  |  |  |  | 215 |  |  |  |  | 220 |  |  |  |  |
| Lys | Asn | Leu | Lys | Thr | Ala | Cys | Asp | Asn | Gly | Lys | Asp | Met | Pro | Ala | Arg |
| 225 |  |  |  |  | 230 |  |  |  |  | 235 |  |  |  |  | 240 |
| Glu | Ala | Met | Ala | Tyr | Ala | Gln | Phe | Leu | Ala | Gly | Met | Ala | Phe | Asn | Asn |
|  |  |  |  | 245 |  |  |  |  | 250 |  |  |  |  | 255 |  |
| Ala | Ser | Leu | Gly | Tyr | Val | His | Ala | Met | Ala | His | Gln | Leu | Gly | Gly | Tyr |
|  |  |  | 260 |  |  |  |  | 265 |  |  |  |  | 270 |  |  |
| Tyr | Asn | Leu | Pro | His | Gly | Val | Cys | Asn | Ala | Val | Leu | Leu | Pro | His | Val |
|  |  | 275 |  |  |  |  | 280 |  |  |  |  | 285 |  |  |  |
| Leu | Ala | Tyr | Asn | Ala | Ser | Val | Val | Ala | Gly | Arg | Leu | Lys | Asp | Val | Gly |
|  | 290 |  |  |  |  | 295 |  |  |  |  | 300 |  |  |  |  |

```
Val Ala Met Gly Leu Asp Ile Ala Asn Leu Gly Asp Lys Glu Gly Ala
305                 310                315                320

Glu Ala Thr Ile Gln Ala Val Arg Asp Leu Ala Ala Ser Ile Gly Ile
            325             330                335

Pro Ala Asn Leu Thr Glu Leu Gly Ala Lys Lys Glu Asp Val Pro Leu
        340             345             350

Leu Ala Asp His Ala Leu Lys Asp Ala Cys Ala Leu Thr Asn Pro Arg
        355             360             365

Gln Gly Asp Gln Lys Glu Val Glu Glu Leu Phe Leu Ser Ala Phe
```

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CTTCTTCAAC TTTTTATATT CCTTTCG        27

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CGGAGGCATT GTTTG        15

The foregoing description of the invention is exemplary for purposes of illustration and explanation. It should be understood that various modifications can be made without departing from the spirit and scope of the invention. Accordingly, the following claims are intended to be interpreted to embrace all such modification.

What is claimed is:

1. A recombinant *Streptococcus mutans* strain characterized by a) a deficiency in lactic acid production and b) production of a recombinant alcohol dehydrogenase.

2. The strain of claim 1, wherein the lactic acid production deficiency is due to a defect in the lactate dehydrogenase gene.

3. The strain of claim 1, wherein the recombinant alcohol dehydrogenase gene is a *Zymomonas mobilis* alcohol dehydrogenase gene.

4. The strain of claim 3, wherein the *Zymomonas mobilis* alcohol dehydrogenase gene encodes alcohol dehydrogenase II.

5. The strain of claim 1, wherein the recombinant alcohol dehydrogenase gene is a *Streptococcus rattus* alcohol dehydrogenase gene.

6. The strain of claim 1, wherein the strain is further characterized by production of a bacteriocin.

7. The strain of claim 6, wherein the bacteriocin has a molecular weight less than 1,000 daltons, and has antibacterial activity against a bacteriocin-susceptible *Streptococcus mutans* strain.

8. The strain of claim 1, wherein the strain is a D-alanine auxotroph.

9. The strain of claim 8, wherein the strain is contains a defect in the alanine racemase gene.

10. The strain of claim 1, wherein the strain is derived from JH1000 or a variant thereof.

11. A recombinant *Streptococcus mutans* strain characterized by: 1) a deficiency in lactic acid production; 2) production of a recombinant alcohol dehydrogenase; and 3) production of a bacteriocin having antibacterial activity against a bacteriocin-susceptible *Streptococcus mutans* strain.

12. The strain of claim 11, wherein the strain is *Streptococcus mutans* JH1000 or a variant thereof.

13. The strain of claim 12, wherein the strain is a *Streptococcus mutans* JH1000 variant that produces bacteriocin at an increased level relative to *Streptococcus mutans* JH1000.

14. The strain of claim 13, wherein the *Streptococcus mutans* JH1000 variant is *Streptococcus mutans* JH1140 or a variant thereof.

15. The strain of claim 11, wherein the strain is a D-alanine auxotroph.

16. The strain of claim 15, wherein the strain has a defect in alanine racemase.

17. *Streptococcus mutans* JH1140 having ATCC Accession No. 55676.

18. A method of reducing the incidence or severity of dental caries in a dental caries-susceptible host comprising administering orally to a dental caries-susceptible host a recombinant *Streptococcus mutans* strain having 1) a recombinant alcohol dehydrogenase gene and 2) a deficiency in lactic acid production, in an amount effective for replacement of dental caries-causing *Streptococcus mutans* host strains in the oral cavity of the host.

19. The method of claim 18, wherein the recombinant *Streptococcus mutans* strain produces a bacteriocin having antibacterial activity against a bacteriocin-susceptible *Streptococcus mutans* strain.

20. The method of claim 18, wherein the lactic acid production deficiency is due to a defect in the lactate dehydrogenase gene.

21. The method of claim 18, wherein the recombinant alcohol dehydrogenase gene is a *Zymomonas mobilis* alcohol dehydrogenase gene.

22. The method of claim 21, wherein the *Zymomonas mobilis* alcohol dehydrogenase gene encodes alcohol dehydrogenase II.

23. The method of claim 18, wherein the recombinant *Streptococcus mutans* strain is a D-alanine auxotroph.

24. The method of claim 23, wherein the recombinant *Streptococcus mutans* strain contains a defect in the alanine racemase gene.

25. The method of claim 18, wherein the recombinant *Streptococcus mutans* strain is contained in a mouthwash, toothpaste, chewing gum, floss, chewable tablet, lyophil, or culture medium.

26. The method of claim 23, wherein the method further comprises administering orally to the host D-alanine in an amount effective to maintain the recombinant *Streptococcus mutans* strain in the oral cavity of the host.

27. The method of claim 26, wherein D-alanine is contained in a mouthwash, toothpaste, floss, chewing gum, or chewable tablet.

28. A pharmaceutical composition for reducing the incidence or severity of dental caries comprising:

a recombinant *Streptococcus mutans* strain having 1) a recombinant alcohol dehydrogenase gene and 2) a deficiency in lactic acid production; and a pharmaceutically acceptable carrier.

29. The composition of claim 28, wherein the recombinant *Streptococcus mutans* strain produces a bacteriocin having antibacterial activity against a bacteriocin-susceptible *Streptococcus mutans* strain.

30. The composition of claim 28, wherein the lactic acid production deficiency is due to a defect in the lactate dehydrogenase gene.

31. The composition of claim 28, wherein the recombinant alcohol dehydrogenase gene is a *Zymomonas mobilis* alcohol dehydrogenase gene.

32. The composition of claim 28, wherein the recombinant *Streptococcus mutans* strain is a D-alanine auxotroph.

33. The composition of claim 32, wherein the recombinant *Streptococcus mutans* strain contains a defect in the alanine racemase gene.

34. The composition of claim 32, wherein the composition further comprises D-alanine.

35. The composition of claim 28, wherein the composition further comprises a flavor-enhancing agent.

36. The composition of claim 28 formulated as a mouthwash, toothpaste, chewing gum, floss, chewable tablet, lyophil, or culture media.

* * * * *